(12) United States Patent
Carreira

(10) Patent No.: US 6,586,644 B2
(45) Date of Patent: Jul. 1, 2003

(54) PROCESS FOR PRODUCING OPTICALLY ACTIVE PROPARGYL ALCOHOLS

(75) Inventor: Erick M. Carreira, ETH Honggerberg, HCI H 335, CH-8093 Zurich (CH)

(73) Assignees: Erick M. Carreira, Zurich (CH); Sumika Fine Chemicals Company, Limited, Osaka (JP)

( * ) Notice: Subject to any disclaimer, the term of this patent is extended or adjusted under 35 U.S.C. 154(b) by 0 days.

(21) Appl. No.: 10/232,386

(22) Filed: Sep. 3, 2002

(65) Prior Publication Data

US 2003/0088100 A1 May 8, 2003

Related U.S. Application Data

(60) Provisional application No. 60/326,983, filed on Oct. 5, 2001.

(30) Foreign Application Priority Data

Mar. 5, 2002 (JP) ........................................ 2002-058625

(51) Int. Cl.[7] .......................... C07C 33/04; C07C 31/18
(52) U.S. Cl. ..................... 568/874; 568/873; 568/855
(58) Field of Search ................................. 568/873, 874, 568/855, 813

(56) References Cited

FOREIGN PATENT DOCUMENTS

CN           1314333 A  *  9/2001

OTHER PUBLICATIONS

Boyall et al., Organic Letters, 2, (2000), pp. 4233–4236.*
Frantz et al., J. Am. Chem. Soc. 122, (2000) pp. 1806.*

* cited by examiner

Primary Examiner—Samuel Barts
Assistant Examiner—Elvis O. Price

(74) Attorney, Agent, or Firm—Fitch, Even, Tabin & Flannery

(57) ABSTRACT

A process for producing an optically active propargyl alcohol represented by the following formula (4):

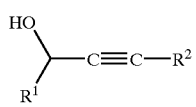

(4)

wherein $R^1$ is an alkyl group, a cycloalkyl group, an alkenyl group, a cycloalkenyl group, an alkynyl group, an alkylsilyl group, an aromatic hydrocarbon group, a C2–C10 heterocyclic group having 1-3 heteroatoms or a C1–C10 alkyl group having 1–3 heteroatoms, and $R^2$ is an alkyl group, a cycloalkyl group, an alkenyl group, a cycloalkenyl group, an alkynyl group, an alkylsilyl group, an aromatic hydrocarbon group, a C2-C10 heterocyclic group having 1–3 heteroatoms or a C1–C10 alkyl group having 1–3 heteroatoms, which comprises allowing an aldehyde compound represented by the following formula (1):

$$R^1\text{—CHO} \qquad (1)$$

to react with an alkyne compound represented by the following formula (2):

$$HC\equiv C\text{—}R^2 \qquad (2)$$

in the presence of an optically active aminoalcohol and a tertiary amine and a zinc halogenated lower alkane sulfonate in an amount of less than equivalent molar base on the aldehyde compound of formula (1): without solvent or with a solvent in an amount of 10-fold by weight or less based on the aldehyde compound of formula (1); and according to the process, high volumetrically efficiency and atomic economy can be attained, the objective optically active propargyl alcohol can be obtained in a high yield and a high enatioselectivity.

11 Claims, No Drawings

PROCESS FOR PRODUCING OPTICALLY ACTIVE PROPARGYL ALCOHOLS

This complete application claims the priority and filing date benefit of U.S. Provisional Application No. 60/326,983, filed Oct. 5, 2001, the complete disclosure of which is incorporated herein by reference.

FIELD OF THE INVENTION

The present invention relates to a process for producing optically active propargyl alcohols useful as synthetic intermediates for medicines, agricultural chemicals or the like. In more detail, it relates to a process for producing optically active propargyl alcohols in which an aldehyde compound and a terminal acetylene are reacted in the presence of an optically active amino alcohol, using a zinc halogenated lower alkane sulfonate as the catalyst.

PRIOR ARTS

Propargyl alcohols have been used as intermediates for various kinds of chemicals. Particularly, increasing their biological activities from their racemates, optically active propargyl alcohols have been known as useful intermediates for medicines, agricultural chemicals, polymeric materials or the like, and efficient production methods of the optically active compounds have been desired to be developed.

As a process for producing optically active propargyl alcohols, there have been reported processes in which a stoichiometric quantity of metal acetylide is added to an aldehyde or a ketone enantioselectively (Journal of American Chemical Society 1994, 116, 3151–3152, Journal of American Chemical Society 1998, 120, 2028). Among other, the processes in which a zinc acetylide is used as the metal acetylide, have been reported many. However, in such a process, a stoichiometric or more quantity of zinc dialkylate, which is unstable in the air, is generally used as the zinc acetylide (Synthesis 1999, 1453–1458, Chem. Rev. 1992, 92, 833–856.). In addition to the above, a process in which an acetylene and an aldehyde are reacted in the presence of an optically active N-methylephedrine and a stoichiometric quantity of zinc containing compound has been known as a process for producing optically active propargyl alcohols (Journal of American Chemical Society 2000, 122, 1806–1807, Organic Letters2000, 2,4233–4236.).

According to the above processes, however, still a sufficient yield of optically active propargyl alcohol and a sufficient enantioselectivity (optical yield) have not been attained, and a production process capable of attaining higher yield and enatioselectivity is desired to be developed.

Further, the above-mentioned known production processes require a stoichiometric quantity of metal reagent, and amount of the used metal is not a truly catalytic quantity. Therefore, it is also desired that the reaction system volume and the amount of starting materials required for the product are made as small as possible, amount of materials to be used and disposals are reduced, and the volumetrically efficiency and atomic economy are improved.

An object of the present invention is to provide a process for producing optically active propargyl alcohols, wherein the metal compound is used in an amount of less than equivalent molar, that is, a truly catalytic quantity of metal is used, and whereby a high yield and a high enantioselectivity of the objective optically active propargyl alcohol can be attained, and the volumetrically efficiency and atomic economy are improved, reducing amount of materials to be used and disposals.

The present inventors have found that, in a process for producing optically active propargyl alcohols by reacting an aldehyde compound and a terminal acetylene in the presence of an optically active amino alcohol, using a zinc halogenated lower alkane sulfonate as the catalyst, when the aldehyde and the terminal acetylene are those having specific structures, (1) the reaction can be carried out even in the absence of solvent or in a small amount of solvent and even by using a zinc halogenated lower alkane sulfonate in an amount of less than equivalent molar, and, as the results, high volumetrically efficiency and atomic economy can be attained, and (2) high yield and a high enatioselectivity of the produced optically active propargyl alcohol can be attained. The present invention was completed based on these findings.

SUMMARY OF THE INVENTION

The present invention provides a process for producing an optically active propargyl alcohol represented by the following formula (4):

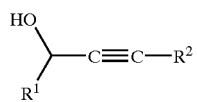

(4)

wherein
$R^1$ is an alkyl group, a cycloalkyl group, an alkenyl group, a cycloalkenyl group, an alkynyl group, an alkylsilyl group, an aromatic hydrocarbon group, a C2–C10 heterocyclic group having 1–3 heteroatoms or a C1–C10 alkyl group having 1–3 heteroatoms, provided that
the alkyl group, the cycloalkyl group, the alkenyl group, the cycloalkenyl group, the alkynyl group, the alkylsilyl group and the C1–C10 alkyl group having 1–3 heteroatoms are unsubstituted or substituted by 1–3 substituents selected from halogen atoms, hydroxyl groups, carboxyl groups, carbonyloxyalkyl groups which may be optionally substituted, carbonyloxyaryl groups which may be optionally substituted, nitro groups, alkyl groups, alkenyl groups, cycloalkyl groups, cycloalkenyl groups, aralkyl groups, alkoxy groups, di-substituted amino groups, aryl groups which may be optionally substituted, C2–C10 heterocyclic groups having 1–3 heteroatoms, C1–C10 alkyl groups having 1–3 heteroatoms and alkylsilyloxy groups, and
the aromatic hydrocarbon group and the C2–C10 heterocyclic group having 1–3 heteroatom are unsubstituted or substituted by 1–3 substituents selected from halogen atoms, hydroxyl groups, carboxyl groups, carbonyloxyalkyl groups which may be optionally substituted, carbonyloxyaryl groups which may be optionally substituted, nitro groups, alkyl groups, alkenyl groups, cycloalkyl groups, cycloalkenyl groups, aralkyl groups, alkoxy groups, amino groups, C1–C10 alkyl groups having 1–3 heteroatoms and alkylsilyloxy groups; and
$R^2$ is an alkyl group, a cycloalkyl group, an alkenyl group, a cycloalkenyl group, an alkynyl group, an alkylsilyl group, an aromatic hydrocarbon group, a C2–C10 heterocyclic group having 1–3 heteroatoms or a C1–C10 alkyl group having 1–3 heteroatoms, provided that
the alkyl group, the cycloalkyl group, the alkenyl group, the cycloalkenyl group, the alkynyl group, the alkylsilyl group, and the C1–C10 alkyl group having 1–3 heteroatoms are unsubstituted or substituted by 1–3 substituents selected from halogen atoms, hydroxyl groups, carboxyl groups, carbonyloxyalkyl groups which may be optionally substituted, carbonyloxyaryl groups which may be optionally substituted, nitro groups, alkyl groups, alkanyl groups, cycloalkyl groups, cycloalkenyl groups, aralkyl groups, acyloxy groups, alkoxy groups, amino groups, groups represented by —ORa wherein Ra represents a C2–C10 heterocyclic group having 1–3 heteroatoms, aryl groups which may be optionally substituted, C2–C10 heterocyclic groups having 1–3 heteroatoms, C1–C10 alkyl groups having 1–3 heteroatoms and alkylsilyloxy groups, and the aromatic hydrocarbon group and the C2–C10 heterocyclic group having 1–3 heteroatoms are unsubstituted or substituted by 1–3 substituents selected from halogen atoms, hydroxyl groups, carboxyl groups, carbonyloxyalkyl groups which may be optionally substituted, carbonyloxyaryl groups which may be optionally substituted, nitro groups, alkyl groups, alkenyl groups, cycloalkyl groups, cycloalkenyl groups, aralkyl groups, alkoxy groups, amino groups, C1–C10 alkyl groups having 1–3 heteroatoms and alkylsilyloxy groups;

which comprises allowing an aldehyde compound represented by the following formula (1).

  (1)

wherein $R^1$ means as defined above,
to react with an alkyne compound represented by the following formula (2):

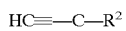  (2)

wherein $R^2$ means as defined above;
in the presence of an optically active aminoalcohol represented by the following formula (3):

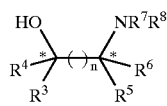  (3)

wherein
$R^3$, $R^4$, $R^5$ and $R^6$ each independently are a hydrogen atom, a C1–C6 alkyl group, a C2–C6 alkynyl group, a C1–C6 alkylsilyl group, a C3–C12 cycloalkyl group, a C2–C10 cyclic amine group or a C6–C10 aryl group, which are unsubstituted or substituted by a C1–C10 alkyl group, a C6–C10 aryl group, a nitro group, an amino group, a halogen atom, a sulfide group or a sulfonyl group, provided that optional two of $R^3$, $R^4$, $R^5$ and $R^6$ may together form a C2–C12 alicyclic ring or a C2–C12 aromatic ring that may incorporate one or more heteroatoms (N,O,S) as linkers and
$R^7$ and $R^8$ each independently are a C1–C6 alkyl group, a C2–C6 alkynyl group, a C1–C6 alkylsilyl group, a C3–C12 cycloalkyl group or a C6–C10 aryl group, or $R^7$ and $R^8$ together form a C3–C12 membered ring or 3–12 membered heterocyclic ring, which are unsubstituted or substituted by a C1–C10 alkyl group, a C6–C10 aryl group, a nitro group, an amino group, a halogen atom, a sulfide group or a sulfonyl group, and n is 0, 1, or 2, and a tertiary amine and a zinc halogenated lower alkane sulfonate in an mount of less than equivalent molar base on the aldehyde compound of formula (1);
without solvent or with a solvent in an amount of 10 -fold by weight or less based on the aldehyde compound of formula (1).

The combination of "C" and "integer" prefixed to names of groups, such as "C1–C10" used above, shows number of carbon atoms. Hereinafter, the same expression is used. For example, "C6–C10" shows that the carbon number is 6–10, and "tri(C1–C4alkyl)silyloxy" means a silyloxy group having 3 alkyl groups each of which has 1–4 carbon atoms. An alkyl group includes not only a straight chain alkyl group but also a branched alkyl group.

DETAILED DESCRIPTION OF THE INVENTION

The aldehyde compound used in the present invention is represented by the formula (1). In the formula (1), $R^1$ represents an alkyl group, a cycloalkyl group, an alkenyl group, a cycloalkenyl group, an alkynyl group, an allylsilyl group, an aromatic hydrocarbon group, a C2–C10 heterocyclic group having 1–3 heteroatoms or a C1–C10 alkyl group having 1–3 heteroatoms.

The alkyl group, the cycloalkyl group, the alkenyl group, the cycloalkenyl group, the alkynyl group, the alkylsilyl group and the C1–C10 alkyl group having 1–3 heteroatoms, which are represented by $R^1$, are unsubstituted or substituted by 1–3 substituents selected from halogen atoms, hydroxyl groups, carboxyl groups, carbonyloxyalkyl groups which may be optionally substituted, carbonyloxyaryl groups which may be optionally substituted, nitro groups, alkyl groups, alkenyl groups, cycloalkyl groups, cycloalkenyl groups, aralkyl groups, alkoxy groups, amino groups, aryl groups which may be optionally substituted, C2–C10 heterocyclic groups having 1–3 heteroatoms, C1–C10 alkyl groups having 1–3 heteroatoms and alkylsilyloxy groups, and the aromatic hydrocarbon group and the C2–C10 heterocyclic group having 1–3 heteroatoms, which are represented by $R^1$, are unsubstituted or substituted by 1–3 substituents selected from halogen atoms, hydroxyl groups, carboxyl groups, carbonyloxyalkyl groups which may be optionally substituted, carbonyloxyaryl groups which may be optionally substituted, nitro groups, alkyl groups, alkenyl groups, cycloalkyl groups, cycloalkenyl groups, aralkyl groups, alkoxy groups, amino groups, C1–C10 alkyl groups having 1–3 heteroatoms and alkylsilyloxy groups.

In the C2–C10 heterocyclic group having 1–3 heteroatoms or a C1–C10 alkyl group having 1–3 heteroatoms, represented by $R^1$ or being a substituent on a group represented by $R^1$, when the heteroatom is a nitrogen atom, it is preferred that the nitrogen atom is substituted, that is, the nitrogen atom does not connect to a hydrogen atom.

The alkyl group, represented by $R^1$ or being a substituent on a group represented by $R^1$, preferably has 1–12 carbon atoms. The cycloalkyl group, represented by $R^1$ or being a substituent on a group represented by $R^1$, preferably have 3–12 carbon atoms. The alkenyl group or alkynyl group, represented by $R^1$ or being a substituent on a group represented by $R^1$, preferably have 2–12 carbon atoms. The cycloalkenyl group, represented by $R^1$ or being a substituent on a group represented by $R^1$, preferably have 4–12 carbon atoms.

As the alkylsilyl group represented by $R^1$ or being a substituent on a group represented by $R^1$, a silyl group connected with one or more C1–C6 alkyl groups is preferred, and, a silyl group connected with three C1–C6 alkyl groups is particularly preferred.

As a substituent on a group represented by $R^1$, the carbonyloxyalkyl group preferably has 2–10 carbon atoms, and may be optionally substituted with a C6–C10 aryl group, a C1–C10 alkyl group or the like.

As a substituent on a group represented by $R^1$, the carbonyloxyaryl group preferably has 7–12 carbon atoms, and may be optionally substituted with a C6–C10 aryl group, a C1–C10 alkyl group or the like.

As the aromatic hydrocarbon group, an aryl group, such as phenyl, is exemplified.

Examples of the C2–C10 heterocyclic group having 1–3 heteroatoms, represented by $R^1$ or being a substituent on a group represented by $R^1$, include saturated and unsaturated heterocyclic group, such as piperidyl, pyridyl, pyrrolidyl, quinolyl, furyl, pyryl, tetrahydrofuranyl, tetrahydropyranyl, and the like.

The alkenyl group, represented by $R^1$ or being a substituent on a group represented by $R^1$, includes an allyl group and the like.

The aralkyl group means an alkyl group substituted by an aryl group, and preferably has about 7–12 carbon atoms.

The alkoxy group preferably has about 1–10 carbon atoms.

As substituents on the amino groups, a C6–C10 aryl group, a C1–C10 alkyl group, a C7–C12 aralkyl group are exemplified.

Examples of substituents on the aryl group include a halogen atom, a hydroxyl group, a carboxyl group, a C2–C10 carboxylate group, a nitro group, a C6–C10 aryl group, a C1–C10 alkyl group, a C7–C12 aralkyl group, a C1—C10 alkoxy group and the like.

As the alkylsilyloxy group, a substituent on a group represented by $R^1$, a silyloxy group connected with one or more C1–C6 alkyl groups is preferred, and, a silyloxy group connected with three C1–C6 alkyl groups is particularly preferred.

Examples of the groups represented by $R^1$ include a C1–C12 alkyl group unsubstituted or substituted by a tri(C1–C12 alkyl) Silyloxy group or one or more C1–C4 alkenyl groups, a C3–C12 cycloalkyl group unsubstituted or substituted by a tri(C1–C12 alkyl)silyloxy group or one or more C1–C4 alkenyl groups, a C6–C10 aryl group unsubstituted or substituted by a C1–C6 alkyl group, a furyl group unsubstituted or substituted by a C1–C6 alkyl group, a C1–C12 1-alkenyl group unsubstituted or substituted by a C6–C10 aryl group, and a piperidyl, pyridyl, pyrrolidyl or quinolyl group in which the nitrogen atom is connected to a substituent selected from C1–C6 alkyl groups and C7–C12 aralkyl groups and which may further optionally be connected to a C1–C6 alkyl group, and the like.

More concrete examples of the groups represented by $R^1$ include n-propyl, n-pentyl, n-heptyl, isopropyl, t-butyl, isobutyl, sec-butyl, hexyl, cyclopropyl, cyclohexyl, cyclooctyl, t-butylmethyl, phenyl, alkylphenyl, phenyletenyl, triisopropylsilyloxyethyl, t-butyldimethylsilyloxyethyl, 2-t-butyldimethylsilyloxypropyl, N-benzyl-4-piperidyl, 1,6-diene-4-heptyl, 1-methyl-1-triisopropylsilyloxymethylethyl, furyl, alkylfuryl, pyridyl, naphthyl, alkylnaphthyl, quinolyl, N-alkyl pyrrolidyl, piperidinyl, piperazinyl, imidazolyl, pyrimidinyl, oxazolyl, isozazolyl, morpholinyl, thiazolyl, isothiazolyl, indolyl, thiophenyl, triazinyl, thienyl, sulfoxide, and the like.

The alkyne compound, the other starting material for the process of the present invention, is a compound represented by the formula (2) and having a triple bond.

$R^2$ in the formula (2) represents an al group, a cycloalkyl group, an alkenyl group, a cycloalkenyl group, an alkynyl group, an alkylsilyl group, an aromatic hydrocarbon group, a C2–C10 heterocyclic group having 1–3 heteroatoms or a C1–C10 alkyl group having 1–3 heteroatoms.

The alkyl group, the cycloalkyl group, the alkenyl group, the cycloalkenyl group, the alkynyl group, the alkylsilyl group and the C1–C10 alkyl group having 1–3 heteroatoms, which are represented by $R^2$, are unsubstituted or substituted by 1–3 substituents selected from halogen atoms, hydroxyl groups, carboxyl groups, carbonyloxyalkyl groups which may be optionally substituted, carbonyloxyaryl groups which may be optionally substituted, nitro groups, alkyl groups, alkenyl groups, cycloalkyl groups, cycloalkenyl groups, aralkyl groups, acyloxy groups, alkoxy groups, amino groups, groups represented by —ORa wherein Ra represents a C2–C10 heterocyclic group having 1–3 heteroatoms, aryl groups which may be optionally substituted, C2–C10 heterocyclic groups having 1–3 heteroatoms, C1–C10 alkyl groups having 1–3 heteroatoms and alkylsilyloxy groups.

The aromatic hydrocarbon group and the C2–C10 heterocyclic group having 1–3 heteroatoms, which are represented by $R^2$, are unsubstituted or substituted by 1–3 substituents selected from halogen atoms, hydroxyl groups, carboxyl groups, carbonyloxyalkyl groups which may be optionally substituted, carbonyloxyaryl groups which may be optionally substituted, nitro groups, alklyl groups, alkenyl groups, cycloalkyl groups, cycloalkenyl groups, aralkyl groups, alkoxy groups, di-substituted amino groups, C1–C10 alkyl groups having 1–3 heteroatoms and alkylsilyloxy groups.

In the C2–C10 heterocyclic group having 1–3 heteroatoms or a C1—C10 alkyl group having 1–3 heteroatoms, represented by 10 or Ra or being a substituent on a group represented by $R^1$, when the heteroatom is a nitrogen atom, it is preferred that the nitrogen atom is substituted, that is, the nitrogen atom does not connect to a hydrogen atom.

The alkyl group, represented by $R^2$ or being a substituent on a group represented by $R^2$, preferably has 1–12 carbon atoms. The cycloalkyl group, represented by $R^2$ or being a substituent on a group represented by $R^2$, preferably have 3–12 carbon atoms. The alkenyl group or alkynyl group, represented by $R^2$ or being a substituent on a group represented by $R^2$, preferably have 2–12 carbon atoms. The cycloalkenyl group, represented by $R^2$ or being a substituent on a group represented by $R^2$, preferably have 4–12 carbon atoms.

As the alkylsilyl group represented by $R^2$ or being a substituent on a group represented by $R^2$, a silyl group connected with one or more C1–C6 alkyl groups is preferred, and, a silyl group connected with three C1–C6 alkyl groups is particularly preferred.

As the aromatic hydrocarbon group, an aryl group, such as phenyl, is exemplified.

Examples of the C2–C10 heterocyclic group having 1–3 heteroatoms, represented by $R^2$ or Ra or being a substituent on a group represented by $R^2$, includes saturated and unsaturated heterocyclic group, such as piperidyl, pyridyl, pyrrolidyl, quinolyl, furyl, pyryl, tetrahydrofuranyl, tetrahydropyranyl, and the like.

The alkenyl group, represented by $R^2$ or being a substituent on a group represented by $R^2$, includes an allyl group and the like.

Examples of the acyloxy group as a substituent on a group represented by $R^2$ include carbonyloxy groups connected to a C6–C10 aryl, a C1–C10 alkyl, a C7–C12 aralkyl group or the like.

As the alkoxy group as a substituent on a group represented by $R^2$, those having about 1–10 carbon atoms are preferred and they may be optionally substituted by C6–C10 aryl or the like.

Examples of the groups represented by $R^2$ include a tri(C1–C4 alkyl)silyloxy group, a hydroxyl group, an acetoxy group, a phenyl group, a di-substituted amino group represented by —$NR^7R^8$ (wherein $R^7$ and $R^8$ each independently represent C6–C10 aryl, C1–C12 alkyl or C7–C12 aralkyl), a C3–C10 cycloalkyl group, a C1–C10 alkyl group which may be optionally substituted by a tetrahydropyranyloxy group or one or more of C1–C6 alkoxy groups, a phenyl group which may be optionally substituted by halogen or a C1–C6 alkyl group, a cyclopentanediene-1yl group which may be optionally substituted by a C1–C6 alkyl group, pyrrolyl or pyridyl in which the nitrogen atom is connected to a substituent selected from C1–C6 alkyl groups and C7–C12 aralkyl groups and which may be further optionally substituted by a C1–C6 alkyl group, a tri(C1–C4 alkyl)silyl group, and the like.

More concrete examples of the groups represented by $R^2$ include dibenzylaminomethyl, 2-phenylethyl, phenyl, 1-methyl-1-trimetyloxyethyl, 1-methyl-1-triisopropylsilyloxyethyl, t-butyldimethylsilyloxymethyl, diethoxymethyl, n-butyl, triethylsilyl, trimethylsilyl, acetoxymethyl, 2-tetrahydrofuranyloxy-2-propyl, 2-tetrahydropyranyloxy-2-propyl, 2-hydroxy-2-propyl, p-bromophenyl, cyclopentanediene-1-yl, pyrrolyl, pyridyl, 2-cyclobutylethyl, 3-cyclobutylpropyl, 3-(N-methyl-N-phenylamino)propyl and the like.

It is particularly preferred that the group represented by $R^2$ is 2-tetrahydrofuranyloxy-2-propyl or 2-tetrahydropyranyloxy-2-propyl, since, in this case, the reaction rate with the aldehyde compound is high.

In the present invention, the amount of the alkyne compound of formula (2) utilized for the process is preferably 1 to 5 moles, more preferably 1 to 1.5 moles, based on 1 male of the aldehyde compound of formula (1).

As the tertiary amine utilized in the present invention, tri(C1–C4)allylamine, cyclic amines such as quinoline may be listed, although tri(C1–C4)alkylamine is usually used. Examples of the tri(C1–C4)alkylamine include triethylamine, trimethylamine, methylethylamine, ethyldiisopropylamine and the like. Among them, triethylamine and ethyldiisopropylamine are preferred. The amount of the tertiary amine is usually 0.04 to 1 mole, preferably 0.08 to 0.6 mole, based on 1 mole of the aldehyde compound of formula (1).

As the alkylsilyl group represented by $R^3$, $R^4$, $R^5$ or $R^6$ in the formula (3), a silyl group connected to one or more C1–C6 alkyl groups is preferred, and particularly a silyl group connected with to C1–C6 alkyl groups is preferred.

As the optically active aminoalcohol of formula (3), an optically active N-methylephedrine is preferably exemplified.

The optically active N-methylephedrine can be (+)-N-methylephedrine or (−)-N-methylephedrine, which is available on the market. When (+)-N-methylephedrine is used, a propargyl alcohol of R-configuration is obtained from cyclohexylaldehyde. When (−)-N-methylephedrine is used, a propargyl alcohol of S-configuration is obtained from cyclohexanecarboxaldehyde.

The amount of the optically active N-methylephedrine is usually 0.01 to 1 mole, preferably 0.02 to 0.3 mole based on 1 mole of the aldehyde compound of formula (1).

In the process of the present inventions the reaction of the aldehyde compound and the alkyne compound is carried out in the presence of a zinc halogenated lower alkane sulfonate in an amount of less than 1 mole based on 1 mole of the aldehyde compound of formula (1). As the zinc halogenated lower alkane sulfonate, zinc triflate (zinc trifluoromethanesulfonate) is preferably exemplified.

Zinc triflate is also available on the market, but it is preferable to use zinc triflate after drying at 100 to 140° C. under reduced pressure. The amount of the zinc triflate is usually 0.005 mole to 0.9 mole, preferably 0.01 to 0.5 mole based on 1 mole of the aldehyde compound of formula (1).

The reaction of the aldehyde compound of formula (1) with the alkyne compound of formula (2) is carried out without solvent or with a solvent in an amount of 10-fold by weight or less based on the amount of the aldehyde compound of formula (1).

Examples of the solvents include hydrocarbon solvents such as toluene, hexane, heptane and the like, chlorobenzene, methyl-t-butylether, diethylether, 1,2-dimethoxyethane, 1,4-dioxane, dichloromethane, tetrahydrofuran, acetonitrile, ethylacetate, and a mixture thereof. Among them, toluene is preferred.

When toluene is used as the solvent and its amount is 1 to 5-fold by weight based on the amount of the aldehyde compound of formula (1), high yield and high enatioselectivity (optical yield ee) are attained. Therefore, the amount range of solvent is preferred.

When a solvent such as toluene is used in an amount of 6-fold by weight or more based on the amount of the aldehyde compound of formula (1), the reaction system separates into two layers and the produced optically active propargyl alcohol is contained in the solvent layer. As the result, taking out of the product after completion of the reaction is easy. Therefore, the amount range of solvent is also preferred.

The reaction of the aldehyde compound of formula (1) with the alkyne compound of formula (2) In the present invention can be carried out by adding the above-mentioned starting materials and solvent, if any, in a reaction vessel and heating them. Addition order of the starting materials and solvent is not limited. For example, the alkyne compound, the tertiary amine and the solvent, if any, are added to a mixture of the zinc halogenated lower alkane sulfonate and the optically active aminoalcohol of formula (3) such as an optically active N-methylephedrine, then the aldehyde compound is added thereto, followed by heating.

The reaction temperature is usually in the range from 0 to 120° C., preferably 20 to 80° C., and the reaction time is usually in the range from 1 to 24 hours, preferably 1 to 10 hours.

After completion of the reaction, the reaction mixture is subjected to usual work-up procedures, such as extraction with a solvent, silica gel column Chromatography, re-crystallization, distillation under reduced pressure and the like to give an objective product, namely optically active propargyl alcohol of formula (4).

An optically active propargyl alcohol of formula (1), thus obtained, can be used as an intermediate for medicines, agricultural chemicals or the like. For example, it can be used as an intermediate for synthesizing antineoplastic antibiotic FR901464, an intermediate for synthesizing Himandravine having antimuscarinic activity, or the like.

A process for producing optically active propargyl alcohols is disclosed in Japanese application 2000–058625, filed Mar. 5, 2002, the complete disclosure of which is incorporated herein by reference.

Hereinafter, the present invention is further illustrated by examples in more detail, although the present invention is not limited in any sense to these examples.

EXAMPLE 1

A 10 mL flask is charged with zinc triflate (144 mg, 0.40 mmol, 20 mol% based on the aldehyde compound mentioned below). Vacuum (0.5 hPa or lower) is applied and the flask is heated to 125° C. overnight. The flask is cooled to 23° C., the vacuum released and (+)-N-methylephedrine (80 mg, 0.44 mmol, 22 mol % based on the aldehyde compound mentioned below) is added. Vacuum (0. 5 hPa or lower) is applied for 0.5 hour and then released. To the flask is added triethylsilylacetylene as the alkyne compound (2.1 mmol, 105 mol % based on the aldehyde compound mentioned below) and triethylamine (102 mg, 1.0 mmol, 50 mol % based on the aldehyde compound mentioned below).

The resulting mixture is stirred for 0.25 hour at 23° C., and then cyclohexanecarboxaldehyde (2.0 mmol) as the aldehyde compound is added. The reaction mixture is stirred at 60° C., for 6 hours.

Thereafter, the reaction mixture is poured directly on to a column of silica gel and purification of the material by chromatography ($SiO_2$: using 20–40% $CH_2Cl_2$ solution in pentane) is carried out. The purification gives (R)-1-cyclohexyl-3-(triethylsilyl)-2-propyn-1-ol, a colorless oil, in 87% yield and 91% ee as determined by HPLC analysis by the 3,5-dinitrobenzoate ester (Chiralcel OD-H, 6% isopropyl alcohol in hexane, 0.3 mL/min, 254 nm, t, 19.2 (major), 21.3 (minor)).

EXAMPLE 2

A 10 mL flask is charged with zinc triflate (144 mg, 0.40 mmol, 20 mol % based on the aldehyde compound mentioned below). Vacuum (0.5 hPa or lower) is applied and the flask is heated to 125° C. overnight. The flask is cooled to 23° C., the vacuum released and (+)-N-methylephedrine (80 mg, 0.44 mmol, 22 mol % based on the aldehyde compound mentioned below) is added. Vacuum (0.5 hPa or lower) is applied for 0.5 hour and then released. To the flask is added 2-trimethylsilyloxy-2-methyl-3-butyn as the alkyne compound (2.1 mmol, 105 mol % based on the aldehyde compound mentioned below) and triethylamine (102 mg, 1.0 mmol, 50 mol % base on the aldehyde compound mentioned below).

The resulting mixture is stirred for 0.25 hour at 23° C., and then cyclohexanecarboxaldehyde (2.0 mmol) as the aldehyde compound is added. The reaction mixture is stirred at 60° C. for 4 hours.

Then, the following steps are carried out for removing the triethylsilyl group. The reaction mixture is diluted with diethylether (3 mL) and tetrahydrofuran (0.1 mL). Thereto, 10% hydrochloric acid (3 mL) is added, and the resulting mixture is stirred for 0.2 hour. The reaction mixture thus obtained is poured into a separating funnel containing diethylether (10 mL), and a separation is carried out. The separated organic layer is washed with 10% hydrochloric acid (3 mL). Then, after combining with the water layer, extraction with diethylether (10 mL) is carried out twice. The organic layer thus obtained is washed with a saturated sodium chloride aqueous solution (10 ml), dried with anhydrous sodium sulfate, and filtered, followed by distillation under a reduced pressure for removing the solvent.

Thereafter, the resultant material is poured on to a column of silica gel and purification of the material by chromatography ($SiO_2$: using 35–40% ethylacetate solution in pentane) is carried out. The purification gives (R)-1-cyclohexyl-4-methyl-2-pentyne-1,4-diol, a colorless solid, in 99% yield and 94% ee as determined by HPLC analysis by the 3,5-dinitrobenzoate ester (Chiralcel AD, 10% isopropyl alcohol in hexane, 0.9 mL/min, 254 nm, t, 26.6 (major), 56.4 (minor)).

EXAMPLE 3

A flask is charged with zinc triflate (324 mg, 20 mol % based on the aldehyde compound mentioned below). Vacuum (0.5 hPa or lower) is applied and the flask is heated to 125° C. for 1 hour. The flask is cooled to 23° C., the vacuum released and (−)-N-methylephedrine (176 mg, 22 mol % based on the aldehyde compound mentioned below) is added. Vacuum (0.5 hPa or lower) is applied for 0.5 hour and then released. To the flask, triethylamine (225 mg, 50 mol % based on the aldehyde compound mentioned below) and 5 mL of toluene (8. 7 fold-by weight base on the aldehyde compound mentioned below) are added, and mixed for 2 hours at 25–30° C. Further, trimethylsilylacetylene as the alkyne compound (120 mol % based on the aldehyde compound mentioned below) is added, and stirred for 0.25 hour at 25–30° C.

Then cyclohexanecarboxaldehyde (4.46 mmol) as the aldehyde compound is added. The reaction mixture is stirred at 48–50° C. for 5.25 hours.

Thereafter, purification and HPLC analysis are carried out according to the same manner as in Example 1, and (S)-1-cyclohexyl-3-(trimethylsilyl)-2-propyn-1-ol is obtained in 87% yield and 97% ee. After completion of the reaction, the reaction mass separates into two layers.

EXAMPLES 4–7

According to the same manner as in Example 3, except that the amount of toluene and the reaction time are changed to as shown in Table 1, (S)-1-cyclohexyl-3-(trimethylsilyl)-2-propyn-1-ol is obtained in yield and optical yield(ee) as shown in Table 1.

TABLE 1

| Example No. | 3 | 4 | 5 | 6 | 7 |
|---|---|---|---|---|---|
| Amount of Toluene (mL) | 5 | 4 | 3 | 2 | 1 |
| (*) | (8.7) | (7.0) | (5.2) | (3.4) | (1.7) |
| Reaction time (Hr) | 5.25 | 5 | 5 | 5 | 5 |
| Yield (%) | 87 | 92 | 87 | 98 | 97 |
| ee (%) | 97 | 98 | 95 | 95 | 92 |
| Phase separation** | 2 layers | 2 layers | 1 layer | 1 layer | 1 layer |

(*) fold-by weight based on the aldehyde compound
**number of the layers after completion of the reaction

EXAMPLE 8

A flask is charged with zinc triflate (545 mg, 3 mol % based on the aldehyde compound mentioned blow). Vacuum (0.5 hPa or lower) is applied and the flask is heated to 125° C. for 2 hours. The flask is cooled to 23° C., the vacuum released and (+)-N-methylephedrine (296 mg, 3.3 mol % based on the aldehyde compound mentioned below) is added. Vacuum (0.5 hpa or lower) is applied for 0.5 hour and then released. To the flask, triethylamine (607 mg, 12 mol % based on the aldehyde compound mentioned below) and 2-(1,1-dimethyl-prop-2-ynyloxy)-tetrahydropyran as the alkyne compound (55 mmol, 110 mol % based on the aldehyde compound mentioned below) are added, and stirred for 0.25 hour at 25–30° C. And then cyclohexanecarboxaldehyde (50 mmol) as the aldehyde compound is added. The reaction mixture is stirred at 50° C. for 20 hours. Then, the distillation under reduced pressure gives (R)-1-cyclohexyl-4-methyl-4-tetrahydropyranyloxy-2-pentyn-1-ol, bp 130° C. (0.04 hPa), a colorless oil, in 82% yield.

The ee is determined and is expected to be comparable with the unprotected product after removal tetrahydropyranyl group by treatment with a mixture of HClO4-MeOH (1:1). The unprotected product,(R)-1-cyclohexyl-4-methyl-2-pentyne-1,4-diol, a colorless solid, is carried out the selective esterification with 3,5-dinitro benzoyl chloride to give the nitrobenzoate ester in 99% ee as determined by HPLC analysis (Chiralcel AD, 10% isopropyl alcohol in hexane, 0.9 mL/min, 254 nm, t, 26.6 (major), 56.4 (minor) ).

In the process for producing optically active propargyl alcohols of the present invention, a zinc halogenated lower alkane sulfonate is used in an amount of less than equivalent molar, and the reaction is carried out even in the absence of solvent or in a small amount of solvent. Further, it is particularly advanced the reaction rate is high and the amount of materials to be used and disposals are reduced when the group represented by $R^2$ is 2-tetrahydrofuranyloxy-2-propyl or 2-tetrahydropyanyloxy-2-propyl as the alkyne. Therefore, so-called volumetrically efficiency and atomic economy are high, and a smaller reaction volume and a smaller amount of starting materials are required than conventional methods. Further, the objective optically active propargyl alcohol can be obtained in a high yield and a high enatioselectivity, even though the reaction is carried out even in the absence of solvent or in a small amount of solvent.

What is claimed is:

1. A process for producing an optically active propargyl alcohol represented by the following formula (4):

(4)

wherein $R^1$ is an alkyl group, a cycloalkyl group, an alkenyl group, a cycloalkenyl group, an alkynyl group, an alkylsilyl group, an aromatic hydrocarbon group, a C2–C10 heterocyclic group having 1–3 heteroatoms or a C1–C10 alkyl group having 1–3 heteroatoms, provided that the alkyl group, the cycloalkyl group, the alkenyl group, the cycloalkenyl group, the alkynyl group, the alkylsilyl group and the C1–$C_{10}$ alkyl group having 1–3heteroatoms are unsubstituted or substituted by 1–3 substituents selected from halogen atoms, hydroxyl groups, carboxyl groups, carbonyloxyalkyl groups which may be optionally substituted, carbonyloxyaryl groups which may be optionally substituted, nitro groups, alkyl groups, alkenyl groups, cycloalkyl groups, cycloalkenyl groups, aralkyl groups, alkoxy groups, di-substituted amino groups, aryl groups which may be optionally substituted, C2–C10 heterocyclic groups having 1–3 heteroatoms, C1–C10 alkyl groups having 1–3 heteroatoms and alkylsilyloxy groups, and the aromatic hydrocarbon group and the C2–C10 heterocyclic group having 1–3 heteroatoms are unsubstituted or substituted by 1–3 substituents selected from halogen atoms, hydroxyl groups, carboxyl groups, carbonyloxyalkyl groups which may be optionally substituted, carbonyloxyaryl groups which may be optionally substituted, nitro groups, alkyl groups, alkenyl groups, cycloalkyl groups, cycloalkenyl groups, aralkyl groups, alkoxy groups, di-substituted amino groups, C1–C10 alkyl groups having 1–3 heteroatoms and alkylsilyloxy groups; and $R^2$ is an alkyl group, a cycloalkyl group, an alkenyl group, a cycloalkenyl group, an alkynyl group, an alklsilyl group, an aromatic hydrocarbon group, a C2–C10 heterocyclic group having 1–3 heteroatoms or a C1–C10 alkyl group having 1–3 heteroatoms, provided that the alkyl group, the cycloalkyl group, the alkenyl group, the cycloalkenyl group, the alkynyl group, the alkylsilyl group and the C1–C10 alkyl group having 1–3heteroatoms are unsubstituted or substituted by 1–3 substituents selected from halogen atoms, hydroxyl groups, carboxyl groups, carbonyloxyalkyl groups which may be optionally substituted, carbonyloxyaryl groups which may be optionally substituted, nitro groups, alkyl groups, alkenyl groups, cycloalkyl groups, cycloalkenyl groups, aralkyl groups, acyloxy groups, alkoxy groups, di-substituted amino groups, groups represented by —OR a wherein Ra represents a C2–C10 heterocyclic group having 1–3 heteroatoms, aryl groups which may be optionally substituted, C2–C10 heterocyclic groups having 1–3 heteroatoms, C1–C10 alkyl groups having 1–3 heteroatoms and alkylsilyloxy groups, and the aromatic hydrocarbon group and the C2–C10 heterocyclic group having 1–3 heteroatoms are unsubstituted or substituted by 1–3 substituents selected from halogen atoms, hydroxyl groups, carboxyl groups, carbonyloxyalkyl groups which may be optionally substituted, carbonyloxyaryl groups which may be optionally substituted, nitro groups, alkyl groups, alkenyl groups, cycloalkyl groups, cycloalkenyl groups, aralkyl groups, alkoxy groups, di-substituted amino groups, C1–C10 alkyl groups having 1–3 heteroatoms and alkylsilyloxy groups;

which comprises allowing an aldehyde compound represented by the following formula (1);

(1)

wherein $R^1$ means as defined above, to react with an alkyne compound represented by the following formula (2):

(2)

wherein $R^2$ means as defined above;

in the presence of an optically active aminoalcohol represented by the following formula (3);

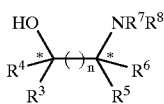

wherein $R^3$, $R^4$, $R^5$ and $R^6$ each independently are a hydrogen atom, a C1–C6 alkyl group, a C2–C6 alkynyl group, a C1–C6 alkylsilyl group, a C3–C12 cycloalkyl group, a C2–C10 cyclic amine group or a C6–C10 aryl group, which are unsubstituted or substituted by a C1–C10 alkyl group, a C6–C10 aryl group, a nitro group, an amino group, a halogen atom, a sulfide group or a sulfonyl group, provided that optional two of $R^3$, $R^4$, $R^5$ and $R^6$ may together form a C2–C12 alicyclic ring or a C2–C12 aromatic ring that may incorporate one or more heteroatoms as linkers and $R^7$ and $R^8$ each independently are a C1–C6 alkyl group, a C2–C6 alkynyl group, a C1–C6 alkylsilyl group, a C3–C12 cycloalkyl group or a C6–C10 aryl group, or $R^7$ and $R^8$ together form a C3–C12 membered ring or 3–12 membered heterocyclic ring, which are unsubstituted or substituted by a C1–C10 alkyl group, a C6–C10 aryl group, a nitro group, an amino group, a halogen atom, a sulfide group or a sulfonyl group, and n is 0, 1, or 2, and a tertiary amine and a zinc halogenated lower alkane sulfonate in an amount of less than equivalent molar base on the aldehyde compound of formula (1); without solvent or with a solvent in an amount of 10-fold by weight or less based on the aldehyde compound of formula (1).

2. The process as recited in claim 1, wherein $R^1$ is n-propyl, n-pentyl, n-heptyl, isopropyl, t-butyl, isobutyl, sec-butyl, hexyl, cyclopropyl, cyclohexyl, cyclooctyl, t-butylmethyl, phenyl, alkylphenyl, phenyletenyl, triisopropylsilyloxyethyl, t-butyldimethylsilyloxyethyl, 2-t-butyldimethylsilyloxypropyl, N-benzyl-4-piperidyl, 1,6-diene-4-heptyl, 1-methyl-1-triisopropylsilyloxymethylethyl, furyl, alkylfuryl, pyridyl, naphthyl, alkylnaphthyl, quinolyl, N-alkyl pyrrolidyl and the like.

3. The process as recited in claim 1, wherein $R^2$ is dibenzylaminomethyl, 2-phenylethyl, phenyl, 1-methyl-1-trimetyloxyethyl, 1-methyl-1-triisopropylsilyloxyethyl, t-butyldimethylsilyloxymethyl, diethoxymethyl, n-butyl, triethylsilyl, trimethylsilyl, acetoxymethyl, 2-tetrahydrofuranyloxy-2-propyl or 2-tetrahydropyranyloxy-2-propyl, 2-hydroxy-2-propyl, p-bromophenyl, cyclopentanediene-1-yl, pyrrolyl, pyridyl, 2-cyclobutylethyl, 3-cyclobutylpropyl and 3-(N-methyl-N-phenylamino)propyl.

4. The process as recited in claim 3, wherein $R^2$ is 2-tetrahydrofuranyloxy-2-propyl or 2-tetrahydropyranyloxy-2-propyl.

5. The process as recited in claim 1, wherein the reaction is conducted under solvent free.

6. The process as recited in claim 1, wherein toluene is used as the solvent.

7. The process as recited in claim 6 wherein toluene amount is 1 to 5-fold by weight based on the amount of the aldehyde compound of formula (1).

8. The process as recited in claim 1, wherein the optically active aminoalcohol of formula (3) is (+) or (−) N-methylephedrine.

9. The process as recited in claim 1, wherein the zinc halogenated lower alkane sulfonate is zinc triflate.

10. The process as recited in claim 9, wherein the amount of zinc triflate is 1 mol % to 50 mole % based on the aldehyde compound of formula (1).

11. The process as recited in claim 1, wherein the tertiary amine is triethylamine or ethyldiisopropylamine.

* * * * *

UNITED STATES PATENT AND TRADEMARK OFFICE
CERTIFICATE OF CORRECTION

PATENT NO. : 6,586,644 B2
DATED : July 1, 2003
INVENTOR(S) : Carreira

It is certified that error appears in the above-identified patent and that said Letters Patent is hereby corrected as shown below:

<u>Column 6,</u>
Line 4, delete "al" and insert -- alkyl --;
Line 37, delete "10 or Ra" and insert -- $R^2$ or Ra --;

<u>Column 7,</u>
Line 18, delete "cyclopentanediene-1yl" and insert -- cyclopentanediene-1-yl --;
Line 41, delete "male" and insert -- mole --;
Line 53, delete "$R^3$, $R^4$ . $R^5$" and insert -- $R^3$, $R^4$, $R^5$ --;

<u>Column 11,</u>
Lines 6-7, delete "cyclohexanecarboxaldehyde" and insert
-- cyclohexanecarboxyaldehyde--;

<u>Column 12,</u>
Line 35, delete "–OR a wherein" and insert -- –ORa wherein --.

Signed and Sealed this

Thirtieth Day of March, 2004

JON W. DUDAS
*Acting Director of the United States Patent and Trademark Office*